United States Patent [19]

Weinstock et al.

[11] 4,216,340

[45] Aug. 5, 1980

[54] PREPARATION OF 5-(2,4-DIFLUOROPHENYL)SALICYLIC ACID AND DERIVATIVES

[75] Inventors: Leonard M. Weinstock, Belle Mead; Arthur S. Wildman, Martinsville; Carl Bagner, Paramus, all of N.J.

[73] Assignee: Merck & Co., Inc., Rahway, N.J.

[21] Appl. No.: 35,149

[22] Filed: May 2, 1979

[51] Int. Cl.² ............................................. C07C 65/78
[52] U.S. Cl. ..................................................... 562/469
[58] Field of Search ......................................... 562/469

[56]  References Cited

U.S. PATENT DOCUMENTS

| 3,714,226 | 1/1973 | Ruyle | 260/473 S |
| 3,992,459 | 11/1976 | Utne et al. | 260/649 F |

FOREIGN PATENT DOCUMENTS

| 907606 | 8/1972 | Canada | 562/469 |
| 1496231 | 12/1977 | United Kingdom | 260/473 S |

Primary Examiner—Paul J. Killos
Attorney, Agent, or Firm—Mario A. Monaco; Raymond M. Speer

[57] ABSTRACT

Improved method of preparing 5-(2,4-difluorophenyl)-salicylic acid and derivatives which favors formation of the desired end product over other undesired isomers, comprising the steps of
(a) diazotizing an aniline compound,
(b) treating the diazonium salt with a salicylic acid ester compound blocked in the 3-position with an easily removed blocking group, preferably cloro,
(c) removing the blocking group, and
(d) hydrolyzing the ester to form the acid final product.

15 Claims, No Drawings

PREPARATION OF 5-(2,4-DIFLUOROPHENYL)SALICYLIC ACID AND DERIVATIVES

BACKGROUND OF THE INVENTION

1. Field of the Invention

The present invention is concerned with an improved method of preparing 5-(2,4-difluorophenyl)salicylic acid and derivatives thereof which favors formation of the desired end product over other undesired isomers. The compound 5-(2,4-difluorophenyl)salicylic acid and derivatives thereof are potent analgesic, anti-inflammatory compounds described in U.S. Pat. No. 3,714,226.

2. Brief Description of the Prior Art

Ruyle et al. U.S. Pat. No. 3,714,226, Jones et al. British Patent Spec. No. 1,496,231, and Utne et al. U.S. Pat. No. 3,992,459 all describe methods of preparing 5-(2,4-difluorophenyl)salicylic acid and derivatives. However, none of these methods suggest the improved method of the present invention which favors formation of the desired end product over other undesired isomers.

SUMMARY OF THE INVENTION

The present invention relates to an improved method of preparing 5-(2,4-difluorophenyl)salicylic acid and derivatives thereof having the formula:

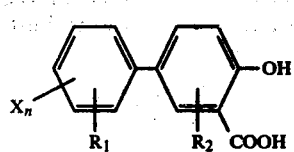

wherein:
$R_1$ is selected from the group consisting of hydrogen, $C_{1-4}$ alkyl, $C_{1-4}$ alkoxy, benzyl, and $C_{1-4}$ alkenyl; $R_2$ is selected from the group consisting of $C_{1-4}$ alkyl and $C_{1-4}$ alkoxy; X is fluoro; and n is 1 to 5.

The above compounds are potent analgesic, anti-inflammatory compounds described in U.S. Pat. No. 3,714,226.

More particularly, the present invention relates to an improved method of preparing compounds of the formula:

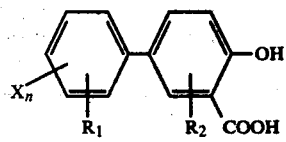

wherein:
$R_1$ and $R_2$ are hydrogen or $C_{1-4}$ alkyl;
X is fluoro; and
n is 2.

Most particularly, the present invention relates to an improved method of preparing the compound 5-(2,4-difluorophenyl)salicylic acid, which has the following structural formula:

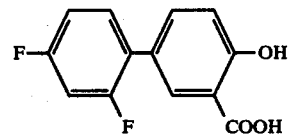

In the improved method of the present invention, one of the starting materials is salicylic acid or derivative which is blocked in the 3-position, as illustrated by the following formula:

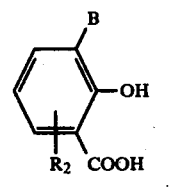

where B represents a blocking group which is easily removed, preferably chloro. Other examples of suitable blocking groups are other halogens, preferably iodo and bromo, and methyl. As a result of this critically placed blocking group, the method of the present inventiont favors formation of the desired end product over other undesired isomers. The method of the present invention is carried out in accordance with the following steps:

(1) The first step of the improved method of the present invention involves diazotization, i.e., it proceeds by way of a diazonium intermediate. This first step may be illustrated as follows for preparation of the preferred 5-(2,4-difluorophenyl)-salicylic acid where the other starting material is 2,4-difluoroaniline:

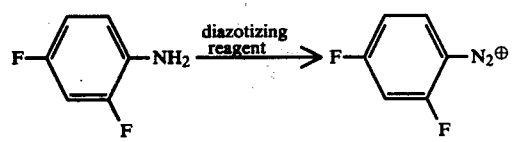

The diazotization may be carried out by employing as the diazotizing reagent one of the following types of compounds: an alkali metal nitrite such as sodium nitrite; a $C_{2-6}$ alkylnitrite such as isopropyl nitrite or isoamyl nitrite; nitrogen trioxide; or nitrogen trioxide/boron trifluoride complex. One of these diazotizing reagents is added to the 2,4-difluoroaniline or derivative starting material contained in an inert solvent such as methylene chloride at room temperature. The reaction is initiated by warming to 60° C.-70° C., when bubbling begins. The reaction mixture is then maintained between ambient and reflux temperatures for 3 to 64 hours. Preferably, the reaction is carried out at reflux temperature for 3 to 8 hours.

A preferred manner of carrying out the diazotization comprises (1) dissolving the 2,4-difluoroaniline or derivative starting material in tetrahydrofuran or a lower alkanol, such as ethanol, propanol or isopropanol; (2) adding to the solution at −5° C. to −10° C. from 1 to 3 molar equivalents of fluoboric acid; (3) mixing the resulting solution with 1 to 3 molar equivalents of a $C_{2-6}$ alkylnitrite, such as isopropyl nitrite or isoamyl nitrite, or an alkali metal nitrite such as sodium nitrite in aqueous solution while maintaining the temperature at −5° C. to 15° C.; and (4) collecting the precipitate of the aryldiazonium fluoborate, such as 2,4-difluorobenzenediazonium fluoborate. These diazonium salts are fairly unstable in the presence of hydroxylic solvents such as water and alcohols. Therefore, they are usually washed well with an alcohol such as isopropanol and a second solvent capable of removing the residual alcoholic solvents, such as ether or methylene chloride. The dry diazonium salt is stable if kept in a dry, cool, dark environment. (2) In the second step of the method of the present invention, the diazonium salt is reacted with the blocked salicylic acid or derivative. This second step may be illustrated as follows:

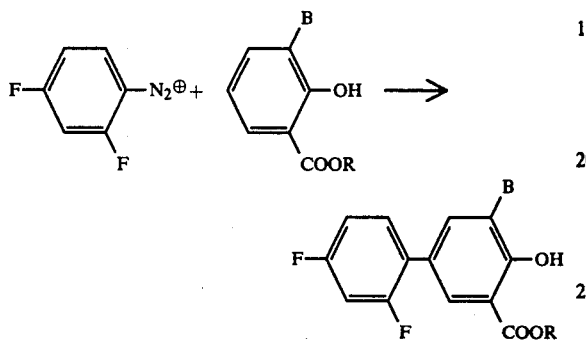

where R is $C_{1-4}$ alkyl, preferably methyl.

In a preferred process, there is combined, on a molar basis, one part of diazonium salt, 0 to 0.5 parts of a strong organic acid such as trichloroacetic or trifluoroacetic acid, 0.1 to 2 parts of copper powder, a finely divided solid such as silica gel, diatomaceous earth, crushed glass, alumina, crushed molecular sieves, magnesium sulfate, or the like, in an excess of the blocked salicyclic acid or derivative, which may also act as a solvent for the reaction. Where the blocked salicylic acid or derivative is a solid, an inert solvent such as methylene chloride may be employed. The reaction is conducted at 5° C. to reflux temperature for 1 to 20 hours, depending on the temperature.

In a preferred alternative, steps (1) and (2) above are carried out together and the diazonium salt is prepared in situ. In this alternative, the process described in the paragraph immediately above is modified by the use of an aniline in place of the diazonium salt, and employing 1.1 to 1.5 parts of a strong organic acid as previously described, as well as a nitrosating agent such as isopropyl nitrite. (3) The third step of the improved method of the present invention involves removal of the blocking group by hydrogenation in the case of a halogen blocking group, or other appropriate method, for example oxidation followed by decarboxylation by heating in the case of the methyl blocking group. Where the blocking group is halogen and the group is removed by hydrogenation, hydrogen is bubbled through the reaction mixture from the preceding step in the presence of a catalyst such as palladium chloride or Raney nickel. This third step may be illustrated as follows:

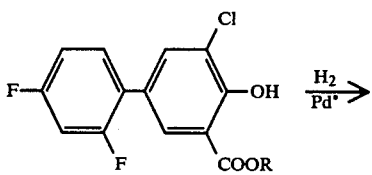

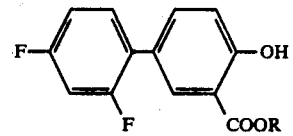

(4) The fourth step of the method of the present invention involves conversion of the salicylate to the corresponding acid. This step is carried out by simple hydrolysis and may be illustrated as follows:

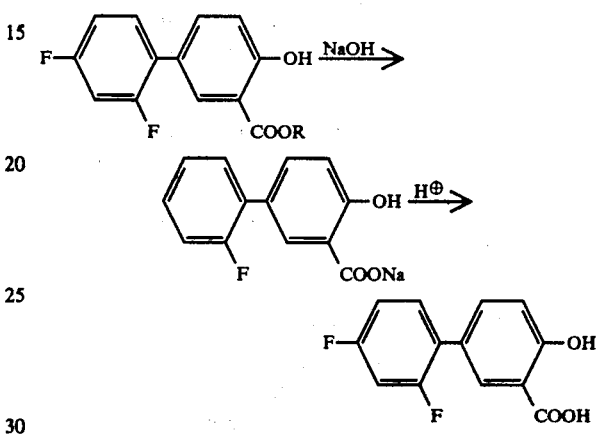

The improved method of the present invention will be better understood from the following illustrative example.

EXAMPLE

The starting material, the methyl ester of 3-chloro-2-hydroxybenzoic acid, may be prepared from 2-chlorophenol using known procedures.

To a reaction flask is added 0.2 g. of copper powder, 25 ml. of methylene chloride, 1 ml. of acetic acid, and 12 g. of methyl 3-chloro-2-hydroxybenzoate, after which the reaction mixture is agitated for 15 minutes. There is then added 1 g. of 2,4-difluorobenzenediazonium fluoborate prepared in accordance with the procedure described in the paragraph immediately below.

A solution of 13 g. of 2,4-difluoroaniline in 30 ml. of isopropanol is chilled to 0° C. and 30 ml. of fluoboric acid (48%) is added. After cooling to 0° C., 9 g. of sodium nitrite in 20 ml. of water is added in a steady stream, with vigorous stirring, keeping the temperature at 5°-10° C. A thick precipitate rapidly forms, the mixture is diluted with 60 ml. of isopropanol, and stirred at 0°-5° C. for 10 min. The precipitate is filtered off, washed well with 100 ml. of cold isopropanol, then with 100 ml. of ether, and vacuum dried to yield 20 g. (88%) of white, crystalline 2,4-difluorobenzenediazonium fluoborate, m.p. 147°-150° C.

The reaction mixture to which the 1 g. of 2,4-difluorobenzenediazonium fluoborate has been added is agitated for 3 hours at 25° C., until nitrogen evolution ceases. The reaction mixture is then filtered to remove the copper salts. The solvent phase of the reaction mixture is washed well with water, and then the solvent is distilled off. The residue is dissolved in 30 ml. of methanol and there is then added 0.1 g. of 5% palladium on carbon catalyst. The reaction mixture is placed in an autoclave under hydrogen pressure for 4 hrs. at 60° C., after which the catalyst is filtered off. The reaction mixture is concentrated by removing most of the methanol, after which the methyl 5-(2,4-difluorophenyl) salicylate crystallizes out. The ester is separated and added to an aqueous solution of 0.5 g. sodium hydroxide and heated to 90° C. for 2 hrs. The reaction mixture is filtered and the pH of the filtrate is adjusted with acid to below 2.0. The resulting solid product 5-(2,4-difluorophenyl) salicylic acid is separated by filtration.

What is claimed is:

1. A method for preparing a compound of the formula:

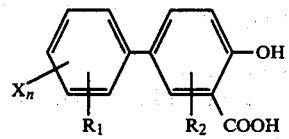

wherein:
R$_1$ is selected from the group consisting of hydrogen, C$_{1-4}$ alkyl, C$_{1-4}$ alkoxy, benzyl, and C$_{1-4}$ alkenyl;
R$_2$ is selected from the group consisting of C$_{1-4}$ alkyl and C$_{1-4}$ alkoxy;
X is fluoro; and
n is 1 to 5;
comprising the steps of
(a) diazotizing a compound of the formula:

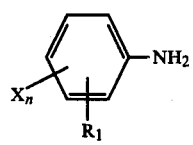

(b) treating the diazonium salt of step (a) with a compound of the formula:

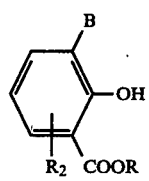

wherein:
B is an easily removed blocking group; and
R is C$_{1-4}$ alkyl;
(c) removing the blocking group B from the product of step (b); and
(d) hydrolyzing the ester of step (c) to form the acid final product.

2. The method of claim 1 wherein B is chloro.

3. The method of claim 1 for preparing 5-(2,4-difluorophenyl) salicylic acid wherein B is chloro and R is methyl.

4. A method for preparing a compound of the formula:

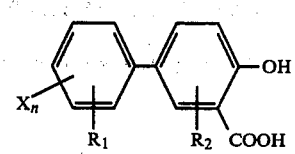

wherein:
R$_1$ is selected from the group consisting of hydrogen, C$_{1-4}$ alkyl, C$_{1-4}$ alkoxy, benzyl, and C$_{1-4}$ alkenyl;
R$_2$ is selected from the group consisting of C$_{1-4}$ alkyl and C$_{1-4}$ alkoxy;
X is fluoro; and
n is 1 to 5; comprising the steps of
(a) diazotizing a compound of the formula:

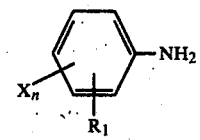

by the steps of
(i) treating a lower alkanol solution of the starting compound at −5° C. to 10° C. with from 1 to 3 molar equivalents of fluoboric acid;
(ii) treating the mixture of step (i) with an aqueous solution of 1 to 3 molar equivalents of a nitrite selected from C$_{2-6}$ alkylnitrite and alkali metal nitrite, while maintaining the temperature at −5° C. to 15° C.; and
(iii) collecting the precipitated aryldiazonium fluoborate;
(b) treating the aryldiazonium fluoborate of step (a) with a compound of the formula:

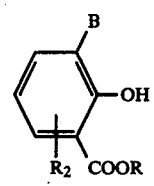

wherein:
B is an easily removed blocking group; and
R is C$_{1-4}$ alkyl;
further in the presence of, on a molar basis, up to 0.5 part of a strong organic acid, 0.1 to 2 parts of copper powder, and an excess of a finely divided inert solid, at a temperature of from 5° C. to reflux for from 1 to 20 hours;
(c) removing the blocking group B from the product of step (b); and
(d) hydrolyzing the ester of step (c) to from the acid final product.

5. The method of claim 4 wherein B is chloro and step (c) is carried out by hydrogenation.

6. The method of claim 4 wherein R is methyl.

7. The method of claim 4 wherein, in step (b) the strong organic acid is trichloroacetic acid or trifluoroacetic acid.

8. The method of claim 4 wherein, in step (b), the finely divided inert solid is selected from silica gel, diatomaceous earth, crushed glass, alumina, crushed molecular sieves, and magnesium sulfate.

9. The method of claim 4 for preparing 5-(2,4-difluorophenyl) salicyclic acid wherein B is chloro and R is methyl.

10. A method for preparing a compound of the formula:

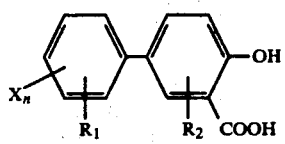

wherein:
R₁ is selected from the group consisting of hydrogen, $C_{1-4}$ alkyl, $C_{1-4}$ alkoxy, benzyl, and $C_{1-4}$ alkenyl;
R₂ is selected from the group consisting of $C_{1-4}$ alkyl and $C_{14}$ alkoxy;
X is fluoro; and
n is 1 to 5; comprising the steps of
(a) treating a compound of the formula:

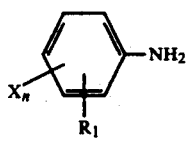

with 1.1 to 1.5 parts, on a molar basis, of a strong organic acid, an aqueous solution of 1 to 3 molar equivalents of a nitrite selected from $C_{2-6}$ alkylnitrite and alkali metal nitrite, 0.1 to 2 parts of copper powder, an excess of finely divided inert solid, and a compound of the formula:

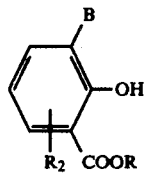

wherein:
B is an easily removed blocking group; and
R is $C_{1-4}$ alkyl;
(b) removing the blocking group B from the product of step (a); and
(c) hydrolyzing the ester of step (b) to form the acid final product.

11. The method of claim 10 wherein, in step (a), the strong organic acid is trichloroacetic acid or trifluoroacetic acid.

12. The method of claim 10 wherein, in step (a), the finely divided inert solid is selected from silica gel, diatomaceous earth, crushed, glass, alumina, crushed molecular sieves, and magnesium sulfate.

13. The method of claim 10 wherein B is chloro and step (b) is carried out by hydrogenation.

14. The method of claim 10 wherein R is methyl.

15. The method of claim 10 for preparing 5-(2,4-difluorophenyl) salicylic acid wherein B is chloro and R is methyl.

* * * * *